US010718771B2

United States Patent
Wu et al.

(10) Patent No.: US 10,718,771 B2
(45) Date of Patent: Jul. 21, 2020

(54) RECOMBINANT BACULOVIRUSES AND THEIR USES IN DETECTING ARTHROPOD-BORNE VIRUS

(71) Applicant: Chung Yuan Christian University, Taoyuan (TW)

(72) Inventors: Tzong-Yuan Wu, New Taipei (TW); Szu-Cheng Kuo, New Taipei (TW); Pei-Yun Shu, Taipei (TW); Chang-Chi Lin, New Taipei (TW); Der-Jiang Chiao, Taoyuan (TW); Ying-Ju Chen, PingTung County (TW); Yi-Ting Lin, Taoyuan (TW); Shu-Fen Chang, Taipei (TW); Chien-Ling Su, Taipei (TW)

(73) Assignee: Chung Yuan Christian University, Taoyuan (TW)

( * ) Notice: Subject to any disclaimer, the term of this patent is extended or adjusted under 35 U.S.C. 154(b) by 0 days.

(21) Appl. No.: 15/892,416

(22) Filed: Feb. 9, 2018

(65) Prior Publication Data

US 2019/0250161 A1 Aug. 15, 2019

(51) Int. Cl.
*G01N 33/569* (2006.01)
*C12N 7/00* (2006.01)
*G01N 33/68* (2006.01)

(52) U.S. Cl.
CPC ......... *G01N 33/56983* (2013.01); *C12N 7/00* (2013.01); *G01N 33/6854* (2013.01); *C12N 2710/14043* (2013.01); *C12N 2770/24122* (2013.01); *C12N 2770/24221* (2013.01); *C12N 2770/36121* (2013.01); *C12N 2770/36221* (2013.01); *C12N 2810/609* (2013.01); *G01N 2333/18* (2013.01); *G01N 2333/181* (2013.01); *G01N 2333/185* (2013.01); *G01N 2333/186* (2013.01); *G01N 2333/19* (2013.01)

(58) Field of Classification Search
CPC ......... G01N 33/56983; G01N 33/6854; G01N 2333/18; C12N 7/00
See application file for complete search history.

(56) References Cited

U.S. PATENT DOCUMENTS

| | | | |
|---|---|---|---|
| 6,190,862 B1 | 2/2001 | Kou et al. | |
| 6,322,781 B1 | 11/2001 | McCutchen | |
| 6,676,936 B1 | 1/2004 | Lai et al. | |
| 2005/0208066 A1* | 9/2005 | Chao | C07K 14/005 424/186.1 |
| 2010/0143406 A1 | 6/2010 | Smith et al. | |

FOREIGN PATENT DOCUMENTS

| | | |
|---|---|---|
| CN | 101792741 A | 8/2010 |
| CN | 102321639 A | 1/2012 |
| CN | 103045544 B | 1/2015 |
| CN | 103585625 B | 12/2015 |
| GB | 2226031 A | 6/1990 |
| TW | 201542199 A | 11/2015 |
| WO | WO2008026225 | 3/2008 |
| WO | WO2016141338 A2 | 9/2016 |

OTHER PUBLICATIONS

Van Oers, M. M., 2011, Opportunities and challenges for the baculovirus expression system, J. Invert. Path. 107:S3-S15.*
Cho, B., et al., 2008, Expression and evaluation of Chikungunya virus E1 and E2 envelope proteins for serodiagnosis of Chikungunya virus infection, Yonsei Med. J. 49(5):828-835.*
Elsevier, Yamaji et al., "Production of Japanese encephalitis virus-like particles using the baculoviruseinsect cell system", pp. 658-659, Jul. 28, 2012, United States.
BioMed Central, Barros et al., "Yellow fever virus envelope protein expressed in insect cells is capable of syncytium formation in lepidopteran cells and could be used for immunodetection of YFV in human sera", pp. 3 and 5, May 27, 2011, United States.
Elsevier, Kuo et al., "Cell-based analysis of Chikungunya virus membrane fusion using baculovirus-expression vectors", pp. 207-209, May 17, 2011, United States.
Yonsei University College of Medicine, Cho et al., "Expression and Evaluation of Chikungunya Virus E1 and E2 Envelope Proteins for Serodiagnosis of Chikungunya Virus Infection", pp. 829-831, Oct. 31, 2008, United States.
Springer, Schuldt et al., "Baculovirus Expression of the Nucleocapsid Protein of a Puumala Serotype Hantavirus", pp. 144-145, 147-148, Mar. 1994, United States.
National Chung Hsing University, Huang, "Development of discriminating ELISA diagnostic reagents to classical swine fever virus (CSFV) and characterization of swine U6 promoter for short hairpin RNA expression", Abstract, pp. 17, 20, 41, 51-53, Jan. 2014, Taichung, Taiwan.
Taiwan Centers for Disease Control, Chang, "Development of rapid test reagent for vector virus", Abstract, pp. 9, 18-20, 2014, Taipei, Taiwan.

* cited by examiner

*Primary Examiner* — Jeffrey S Parkin (57) ABSTRACT

Disclosed herein are recombinant baculoviruses suitable for detecting the presence of arthropod-borne viruses in a biological sample of a test subject. The information derived from the detection may also be used to render a diagnosis on whether the test subject is infected with the arthropod-borne viruses or not, so that proper course of treatment may be assigned to the subject.

4 Claims, 4 Drawing Sheets
(1 of 4 Drawing Sheet(s) Filed in Color)

(A)

vAc-CHIKV-26S-Rhir-EGFP

| P_PH | Capsid | E3 | E2 | 6k | E1 | Stop — Rhir — EGFP Stop |

vAc-JEV-preM-E-Rhir-EGFP

[P_PH] → preM-E (JEV) — Stop — Rhir — EGFP — Stop (B)

| | BV-JEV-prME | JEV | BV-JEV-prME | BV-JEV-prME |
|---|---|---|---|---|
| Abs 405 nm | ~0.25 | ~3.95 | ~2.65 / ~2.35 | ~0.25 / ~0.3 |
| | Nserum | JEV infected serum | | CHIKV infected serum |

vAc-ZIKV-preM-E-Rhir-EGFP $P_{PH}$ — preM-E (ZIKV) — Stop — Rhir — EGFP — Stop (B)

vAc-DENV I-preM-E-Rhir-EGFP $P_{PH}$ — preM-E (DENV I) — Stop — Rhir — EGFP — Stop vAc-DENV II-preM-E-Rhir-EGFP $P_{PH}$ — preM-E (DENV II) — Stop — Rhir — EGFP — Stop

FIG 4

RECOMBINANT BACULOVIRUSES AND THEIR USES IN DETECTING ARTHROPOD-BORNE VIRUS

BACKGROUND OF THE INVENTION

1. Field of the Invention

The present disclosure relates to recombinant baculoviruses. More particularly, the disclosure relates to a recombinant baculovirus having at least one viral proteins of an arthropod-borne virus expressed thereon, and its uses in detecting arthropod-borne virus in biological samples.

2. Description of Related Art

Many of disease-causing organisms are carried by or bred within insects or other arthropods, such as spiders, mites and ticks, and myriapods. Since many of these insects or arthropods bite humans and livestock, as well as damage plants, they transmit a wide variety of diseases, and result in loss of lives and economic damages. Arthropod-born infections, including those such as malaria, dengue fever, Japanese encephalitis, Chikungunya fever and etc, are transmitted by mosquitoes, and are often serious resulting in significant morbidity and even death.

Presently, most methods of detecting arthropod-borne pathogens involve cultivating and isolating the pathogens from their hosts and sequencing the pathogens' DNA to confirm their identities. Since many of these pathogens are highly contagious and lethal, to protect the first-line operator, the isolation and identification must be performed in facilities that comply with at least level 2 biocontainment precautions. Furthermore, cultivating and isolating the pathogens is time-consuming, and DNA sequencing requires well-trained technician and sophisticated equipment, rendering the present detecting methods unsuitable for use in the clinical facility or in the field.

In some cases, purified arthropod-borne viral proteins are used as antigens for detecting the arthropod-borne viruses. Similar to the detecting method described above, producing purified viral proteins is not only time-consuming but also labor intensive, thus is not an economically efficient way for use in the field.

In view of the above, there exist in this art a need of a safe and easy-to-use agents and/or methods for detecting the arthropod-borne viruses, particularly the dangerous and lethal arthropod-borne viruses, such agents and/or methods do not require P2 level facility, nor the expensive and fragile DNA sequencing equipment, while at the same time may provide a result in a much shorter time frame, so that treatments and/or quarantine may be deployed in a timely manner to treat the infected subject and prevent the diseases and/or pathogens from spreading.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure relates in general to the control of human disease transmitted by contact with arthropods. Arthropods such as insects and ticks act as vectors of human disease when they become physically associated with the pathogen or biologically infected by the pathogen. The present disclosure is based on the discovery that a recombinant baculovirus bearing at least one viral protein of an arthropod-borne pathogen, particularly the pathogen that requires at least level 2 biocontainment precautions, on its envelop, may serve as antigens for the detection of such highly lethal pathogens. Accordingly, the recombinant baculovirus of the present disclosure provides a fast, safe, easy-to-use and economical efficient tool for detecting such pathogens without putting the first line operators at risk of being exposed to such highly dangerous pathogens. Further, the detection also serves the purpose of rendering early diagnosis on whether a test subject is infected with such pathogen, so that necessary steps (e.g., medicaments, quarantine and etc) may be timely deployed to treat the subject and to contain the disease or pathogen from spreading.

Accordingly, the first aspect of the present disclosure is directed to a recombinant baculovirus, which is characterized in having at least one viral protein of an arthropod-borne virus expressed on its envelop.

According to embodiments of the present disclosure, the arthropod-borne virus may be a specie of Asfarviridae, Rhabdoviridae, Bunyaviridae, Flaviviridae, Orthomyxoviridae, Reoviridae, or Togaviridae family.

In one embodiment, the arthropod-borne virus is Asfivirus of the Asfarviridae family.

In some embodiments, the arthropod-borne virus is a specie of the Flaviviridae family selected from the group consisting of dengue virus (DENV), hepatitis C virus, Japanese encephalitis virus (JEV), pegivirus, West Nile virus, yellow fever virus (YFV), and Zika virus (ZIKV).

According to some preferred embodiments of the present disclosure, the viral protein of the Flaviviridae family, including but are not limiting to, pre-M, E and a combination thereof.

In certain embodiment, the recombinant baculovirus has at least one JEV viral protein expressed on its envelop. In another embodiment, the recombinant baculovirus has at least one DENV viral protein expressed on its envelop. In still another embodiment, the recombinant baculovirus has at least one ZIKV viral protein expressed on its envelop.

In some embodiments, the arthropod-borne virus is a specie of the Togaviridae family selected from the group consisting of Barmah Forest virus, Chikungunya virus (CHIKV), Eastern equine encephalitis virus, O'nyong-nyong virus, Ross River virus, Rubella virus, Semliki Forest virus, Sindbis virus, Western equine encephalitis virus, and Venezulean equine encephalitis virus.

According to some embodiments of the present disclosure, the viral protein of the Togaviridae family, including but are not limiting to, E, E1, E2, E3 and a combination thereof.

In one preferred embodiment, the arthropod-borne virus is CHIKV; and the present recombinant baculovirus has the CHIKV viral proteins E1 and E2 expressed on its envelop, thus is useful for capturing antibodies of CHIKV present in a biological sample, such as a serum of a CHIKV infected subject.

According to other embodiments of the present disclosure, the viral protein of the Flaviviridae family. Including but are not limiting to, Pre-M, E and a combination thereof.

In another preferred embodiment, the arthropod-borne virus is JEV; and the present recombinant baculovirus has the JEV viral proteins Pre-M and E expressed on its envelop, thus is useful for capturing antibodies of JEV present in a biological sample, such as a serum of a JEV infected subject.

The second aspect of the present disclosure is directed to a method of detecting an arthropod-borne virus in a biological sample. The method includes steps of, mixing the biological sample with the present recombinant baculovirus; and detecting a complex formed between an antibody of the arthropod-borne virus present in the biological sample and the recombinant baculovirus, in an immunological assay.

According to embodiments of the present disclosure, the antibody may be an IgM or IgG.

According to embodiments of the present disclosure, the immunological assay may be an enzyme-linked immunosorbent assay (ELISA) assay.

Exemplary biological sample suitable for use in the present method includes, but is not limited to, a whole blood sample, a plasma sample, a serum sample, a urine sample, a mucus sample, and purified or filtered forms thereof. Preferably, the biological sample is a serum sample.

According to embodiments of the present disclosure, the arthropod-borne virus is a specie of Asfarviridae, Rhabdoviridae, Bunyaviridae, Flaviviridae, Orthomyxoviridae, Reoviridae, or Togaviridae family.

In some embodiments, the arthropod-borne virus is a specie of the Flaviviridae family selected from the group consisting of dengue virus (DENV), hepatitis C virus, Japanese encephalitis virus (JEV), pegivirus, West Nile virus, yellow fever virus (YFV), and Zika virus (ZIKV). In certain embodiment, the recombinant baculovirus has at least one DENV viral protein expressed on its envelop. In another embodiment, the recombinant baculovirus has at least one JEV viral protein expressed on its envelop.

In other embodiments, the arthropod-borne virus is a specie of the Togaviridae family selected from the group consisting of Barmah Forest virus, Chikungunya virus (CHIKV), Eastern equine encephalitis virus, O'nyong-nyong virus, Ross River virus, Rubella virus, Semliki Forest virus, Sindbis virus, Western equine encephalitis virus, and Venezulean equine encephalitis virus.

In one preferred embodiment, the method comprises steps of, mixing a serum sample of a test subject with a recombinant baculovirus having the viral proteins E1 and E2 of CHIKV expressed thereon; and detecting a complex formed between the antibodies of CHIKV present in the serum sample and the recombinant baculovirus by use of an immunogenic assay, such as ELISA.

In another preferred embodiment, the method comprises steps of, mixing a serum sample of a test subject with a recombinant baculovirus having the viral proteins Pre-M and E of JEV expressed thereon; and detecting a complex formed between the antibodies of JEV present in the serum sample and the recombinant baculovirus by use of an immunogenic assay, such as ELISA.

The third aspect of the present disclosure is directed to a kit suitable for detecting an arthropod-borne virus in a biological sample. The kit includes at least, a reagent for detecting an antibody of the arthropod-borne virus present in the biological sample, wherein the reagent comprises the present recombinant baculovirus; a container for housing the reagent; and a legend associated with the container and indicating how to use the present recombinant baculovirus to detect the antibody present in the biological sample.

According to preferred embodiments of the present disclosure, the antibody is an IgM or IgG.

Exemplary biological sample suitable for use in the present method includes, but is not limited to, a whole blood sample, a plasma sample, a serum sample, a urine sample, and a mucus sample. Preferably, the biological sample is a serum sample.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless defined otherwise, all technical and scientific terms used herein have the same meaning as commonly understood by one of the ordinary skill in the art to which this invention belongs.

Provided herein are recombinant baculoviruses, methods and kits for detecting anthropod-borne pathogens such as Togaviruses, including Chikungunya virus (CHIKV), Eastern equine encephalitis virus, O'nyong-nyong virus, Ross River virus, Rubella virus, Sindbis virus, and etc; and Flaviviruses, including, Japanese encephalitis virus (JEV), yellow fever virus (YFV), Zika virus (ZIKV) and etc.

1. Definitions

The term "anthropod-borne virus" are used herein to refer to all viruses that directly or indirectly cause disease in humans through direct or indirect contact with an arthropod, which is physically associated with or biologically infected by the pathogen.

The term "baculoviruses" as used herein refer to arthropod-specific, double stranded DNA viruses that can be used to control insect pests. The nuclear polyhedrosis viruses ("NPV") are one baculovirus subgroup. Various baculoviruses, including those that infect cotton bollworm, *Helicoverpa zea*, tobacco bud worm, *Heliothis virescens*, Douglas fir tussock moth, *Orygia pseudotsugata*, gypsy moth, *Lymantria dispar*, alfalfa looper, *Autographa californica*, European pine sawfly, *Neodiiprion sertifer*, and codling moth, *Cydia pomonella*, are suitable as the vectors for expressing viral proteins of other arthropod-borne viruses, that is, other than baculoviruses themselves, and preferably those that are regarded as dangerous and lethal arthropod-borne viruses. In general, baculoviruses with wide host range are preferred, such as *Autographa californica* multiple nucleopolyhedrovirus (AcMNPV). Examples of baculovirus suitable for use in the present invention include, but are not limited to, AcMNPV, *Anagrapha falclfera* MNPV (AfM-NPV), *Anticarsia gemmatalis* MNPV (AgMNPV), *Bombyx mori* MNPV (BmMNPV), *Buzura suppressaria* single nucleopolyhedrovirus (BsSNPV), *Helicoverpa armigera* SNPV (HaSNPV), *Helicoverpa zea* SNPV (HzSNPV), *Lymantria dispar* MNPV (LdMNPV), *Orgyia pseudotsugata* MNPV (OpMNPV), *Spodoptera frupperda* MNPV (SfMNPV), *Spodoptera exigua* MNPV (SeMNPV), and *Trichoplusia ni* MNPVMNPV).

The term "antigen" as used herein is well understood in the art and includes substances which are immunogenic, i.e., immunogens, as well as substances which induce immunological unresponsiveness, i.e., a lack of reactions by the body's defense mechanisms to foreign substances. As used herein, the term "antigen" is intended to mean full length proteins as well as peptide fragments thereof containing or comprising epitope.

The term "subject" or "patient" is used interchangeably herein and is intended to mean a mammal including the human species that is susceptible to infection by an arthropod-borne virus. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In a preferred embodiment, the subject is a human.

The term "biological sample" as used herein refers to a whole blood sample, a plasma sample, a serum sample, a urine sample, and a mucus sample collected from a mammal, which includes human that has or is suspected of having an infection caused by an arthropod-borne virus. The biological sample can be diluted or undiluted before being subject to the detection of the present recombinant baculoviruses, kits and/or method. In the case when antibody against the arthropod-borne virus are present in the biological sample, the present recombinant baculovirus present in the kit and/or method will specifically bind with the antibody thereby forming a complex that is detected in an immunogenic assay (e.g., ELISA). By contrast, if the antibody against the arthropod-borne virus are not present in the biological sample, then the present recombinant baculoviruses comprised in the present kit and/or method will not bind with the antibody, therefore no immunocomplex is formed.

The singular forms "a," "and," and "the" are used herein to include plural referents unless the context clearly dictates otherwise. Other than in the operating examples, or where otherwise indicated, all numbers expressing quantities of ingredients, reaction conditions, and so forth used in this application are to be understood as being modified in all instances by the term "about." Accordingly, unless the contrary is indicated, the numerical parameters set forth in this application are approximations that may vary depending upon the desired properties sought to be obtained by the present invention.

2. The Recombinant Baculovirus

The present disclosure aims at providing a recombinant baculovirus that serves as antigens for capturing antibodies of a lethal pathogen, particularly the pathogen that requires at least level 2 biocontainment precautions, in a biological sample. By use of the recombinant baculovirus of the present disclosure, the need of expensive level 2 facility, the time-consuming sequencing procedures of the conventional detecting method (e.g., RT-PCT) that requires well-trained technician and sophisticated equipment for confirming the identity of the pathogen are eliminated. Most importantly, the recombinant baculovirus of the present disclosure will ensure the first line operator is free from exposure to highly dangerous pathogens as is common in the existing method for detecting such pathogens. Accordingly, the present recombinant baculovirus offers a safe, fast, easy-to-use, and economically efficient tool for detecting highly dangerous pathogens, particularly, highly dangerous arthropod-borne virus. In addition, the detection also serves the purpose of rendering early diagnosis on whether a test subject is infected with such lethal pathogen, so that necessary steps (e.g., medicaments, quarantine and etc) may be timely deployed to treat the subject and to contain the disease or pathogen from spreading.

Accordingly, the first aspect of the present disclosure is directed to a recombinant baculovirus, which is characterized in having at least one viral protein (e.g., a structural protein or a membrane protein) of an arthropod-borne virus expressed on its envelop.

To produce the present recombinant baculovirus, gene cassettes carrying the viral protein(s) of an arthropod-borne virus of interest are independently constructed and linked to a suitable promoter, so that a baculoviral transfer vector is produced; the transfer vector is then used with the baculoviral DNA to co-transfect a host cell (e.g., an insect cell) to produce the recombinant baculovirus of the present disclosure.

According to embodiments of the present disclosure, the arthropod-borne virus may be a specie of Asfarviridae, Rhabdoviridae, Bunyaviridae, Flaviviridae, Orthomyxoviridae, Reoviridae, or Togaviridae family. Exemplary species of arthropod-borne virus may be Asfivirus of the Asfarviridae family; dengue virus (DENV), hepatitis C virus, Japanese encephalitis virus (JEV), pegivirus, West Nile virus, yellow fever virus (YFV), or Zika virus (ZIKV) of the Flaviviridae family; or Barmah Forest virus, Chikungunya virus (CHIKV), Eastern equine encephalitis virus, O'nyong-nyong virus, Ross River virus, Rubella virus, Semliki Forest virus, Sindbis virus, Western equine encephalitis virus, or Venezulean equine encephalitis virus of the Togaviridae family.

According to embodiments of the present disclosure, the viral protein may be a structural protein or a membrane protein of the arthropod-borne virus. Examples of suitable viral protein of the Togaviridae family, including but are not limiting to, E, E1, E2, E3 and a combination thereof. Examples of suitable viral protein of the Flaviviridae family, including but are not limiting to, Pre-M, E and a combination thereof.

In one preferred embodiment, gene cassettes carrying the nucleotide sequences of viral proteins E1, E2, and E3 of CHIKV (i.e. the cDNA of 26S subgenomic RNA) are respectively constructed and operably linked to a promoter to produce a recombinant baculoviral transfer vector. Promoters suitable for constructing the recombinant baculoviral transfer vector include, but are not limited to, polh promoter (polyhedrin gene promoter), baculovirus-derived promoters, *Bombyx mori*-derived actin promoters, CMV promoters, or chicken 1-actin promoters combined with CMV enhancers (CAG promoters). The baculovirus-derived promoter may be any of 1E1 promoter, 1E2 promoter, p6.9 promoter, VP39 promoter, or p10 promoter. In one preferred embodiment of the present disclosure, polh promoter is employed to construct the recombinant baculoviral transfer vector.

According to preferred embodiments of the present disclosure, the thus produced recombinant baculoviral transfer vector is then co-transfected with a Bac-N-Blue viral DNA into an insect host cell. The Bac-N-Blue viral DNA provides the necessary viral backbone, which contains the propagation-essential genes. Homologous recombination between the recombinant baculoviral transfer vector and the Bac-N-Blue viral DNA in the insect host cell allows the generation of a recombinant baculovirus, which is capable of propagating in the insect host cell and thereby producing the exogenous proteins respectively encoded by the expression gene cassettes (e.g., viral proteins E1, E2, and/or E3 of CHIKV). The recombinant baculovirus was further selected and purified, such as by following the expression of a reporter polypeptide. Suitable insect host cell that may be used in the present disclosure includes, but is not limited to, *S. furpperda* IPBL-9 (Sf9) cell, Sf21 cell, High Five cell, and Minic Sf9 cell. According to preferred embodiments of the present disclosure, the insect host cell is Sf21 cell. Optionally, reporter polypeptides are included in the baculoviral vectors. Examples of reporter polypeptide include, but are not limited to, blue fluorescence protein (BFP), cyan fluorescence protein (CFP), *Discosoma* sp. red fluorescent protein (DsRed), green fluorescence protein (GFP), enhanced green fluorescence protein (EGFP), enhanced yellow fluorescence protein (EYFP), and etc. In some preferred embodiments of the present disclosure, the reporter polypeptide is EGFP. It should be noted that the reporter polypeptide (e.g., EGFP) is not a necessary feature for the aim of this invention, which is, capturing the anti-arthropod-borne virus antibodies that might be present in a biological sample.

The thus produced recombinant baculovirus will have at least one viral protein (i.e., structural protein(s)) of the arthropod-borne virus expressed on its envelop. In one preferred embodiment, the recombinant baculovirus has at least one viral protein of CHIKV (i.e., E1 and E2 of CHIKV) expressed thereon. In another preferred embodiment, the recombinant baculovirus has at least one viral protein of DENV (i.e., pre-M and E of DENV) expressed thereon. In a further preferred embodiment, the recombinant baculovirus has at least one viral protein of JEV (i.e., pre-M and E of JEV) expressed thereon. In still further preferred embodiments, the recombinant baculovirus has at least one viral protein of ZIKV (i.e., pre-M and E of ZIKV) expressed thereon.

3. Application of the Present Recombinant Baculovirus to Detect Arthropod-Borne Viruses The recombinant baculovirus constructed in accordance with the methods described above has at least one viral protein of the arthropod-borne virus expressed on its envelop, accordingly, the entire recombinant baculovirus per se may serve as antigens for capturing antibodies of the interested arthropod-borne virus, if any, in a biological sample.

Thus, another aspect of the present disclosure aims at providing a method of detecting an arthropod-borne virus in a biological sample. The method includes steps of:

mixing the biological sample with the present recombinant baculovirus; and detecting a complex formed between an antibody against the arthropod-borne virus in the biological sample and the recombinant baculovirus, in an immunological assay.

In one preferred embodiment, a serum sample of a hum subject is mixed with a recombinant baculovirus having viral proteins E1 and E2 of CHIKV expressed on its envelop. Accordingly, if the human subject was infected with CHIKV, then the antibodies in the serum will bind with the viral proteins E1 or E2 of CHIKV expressed on the envelop of the recombinant baculovirus and forms a complex.

Exemplary assays suitable for detecting the antigen-antibody complex formed in the present method include, but are not limited to, radioimmunoassay, enzyme-linked immunosorbent assay (ELISA), "sandwich" immunoassay, in situ immunoassays (e.g., using colloidal gold, enzyme or radioisotope labels), dot blot, agglutination assay (e.g., gel agglutination assay, hemagglutination assay and etc), complement fixation assay, immunofluorescence assay, and immunoelectrophoresis assay and etc. In one embodiment, antibody binding is detected by use of ELISA. In one embodiment, the antibody comprises an immunoglobulin M (IgM). In another embodiment, the antibody comprises an immunoglobulin G (IgG).

According to embodiments of the present disclosure, antibodies are detected in bodily fluids, including but are not limited to whole blood, serum, plasma, mucus, urine and purified or filtered forms thereof. In one preferred example, antibodies were detected from a plasma sample. In other embodiments, antibodies are detected from a serum sample.

4. Kits for Detecting Detect Arthropod-Borne Viruses

To provide those skilled in the art tools to use the present invention, the recombinant baculovirus of the present disclosure are assembled into kits for the diagnosis, detection or confirmation of the arthropod-borne virus of interest. In preferred embodiments, the presence of antibodies reactive to the recombinant baculovirus of the present disclosure is used to provide prognosis to a subject. For example, the detection of high level of antibodies reactive to the recombinant baculovirus of the present disclosure, as compared to controls, in a sample, is an indicative of infection of the arthropod-borne virus of interest. The information provided is also used to direct the course of treatment or necessary quarantine means to prevent the disease or the pathogen from spreading. For example, if a subject is found to have antibodies against the recombinant baculovirus of the present disclosure, therapies for the treatment of the disease caused by the arthropod-borne virus may be started at an earlier time when they are more likely to be effective, while necessary steps to contain the pathogen from spreading may also be conducted at the same time.

In one embodiment, the present invention provides a kit for detecting and/or diagnosis an arthropod-borne virus of interest (e.g., CHIKV, JEV, ZIKV and etc) by use of the present recombinant baculovirus. The components included in the kits are: a container, reagents for detecting an antibody in a biological sample, wherein the reagents comprise the present recombinant baculovirus produced in accordance with the procedure described in one example of this invention, the recombinant baculovirus has at least one viral protein of an arthropod-borne virus of interest expressed on its envelop; and a legend associated with the container and indicating how to use the recombinant baculovirus for detecting the antibody in a biological sample. The legend may be in a form of pamphlet, CD, VCD or DVD. The kit may further comprise a negative control that indicates the normal level of the antibody that forms a complex with the recombinant baculovirus in a healthy subject.

The following examples are provided to illustrate the present invention without, however, limiting the same thereto.

EXAMPLES

Example 1 Detecting Anti-CHIKV Antibodies by Use of a Recombinant Baculovirus Having CHIKV Viral Proteins Expressed Thereon 1.1 Construction of vAc-CHIKV26S-Rhir-EGFP The backbones of baculovirus transfer vectors (pBac-Rhir-E) and pBac-CHIKV-26S-Rhir-E plasmid containing the full-length cDNA of the CHIKV 26S subgenomic RNA were constructed as previously described by Kuo et al (J Virol Methods 2011, 175:206-215).

The IPBL-Sf21 (Sf21) cell line was seeded at the density of $2\times10^5$ cells per well in a 24-well plate and cultured in Sf-900 II insect medium that contained 8% heat-inactivated fetal calf serum (FCS) at 27° C. For transfection, a transfection solution containing 1 µg of the pBac-CHIKV-26S-Rhir-E plasmid, 2.5 µL of the linearized viral DNA Bac-N-Blue (Invitrogen, Carlsbad, Calif., USA), 4 µL of Cellfectin (Invitrogen, Carlsbad, Calif., USA) and 350 µL of the serum-free TNM-FH medium was added to each well. After being culture at 27° C. for 5 hrs, the transfection solution in each well was replaced by 350 µL of the TNM-FH medium supplemented with 10% FCS and continued to culture at 27° C. for additional 72 hrs.

Recombinant baculoviruses were collected from Sf21 cell cultures that emitted green fluorescence under a fluorescence microscope (Nikon, Tokyo, Japan). Recombinant baculoviruses (i.e., the vAc-CHIKV26S-Rhir-EGFP, FIG. 1, panel A) were purified by end-point dilutions. The viral titer was determined by end-point dilution and fluorescence detection in a 96-well plate, and was calculated by use of the 50% tissue culture infectious dose ($TCID_{50}$) method. Sequences of all recombinant viruses were confirmed by viral DNA sequencing.

1.2 Characterization of vAc-CHIKV26S-Rhir-EGFP of Example 1.1

Figure 1:
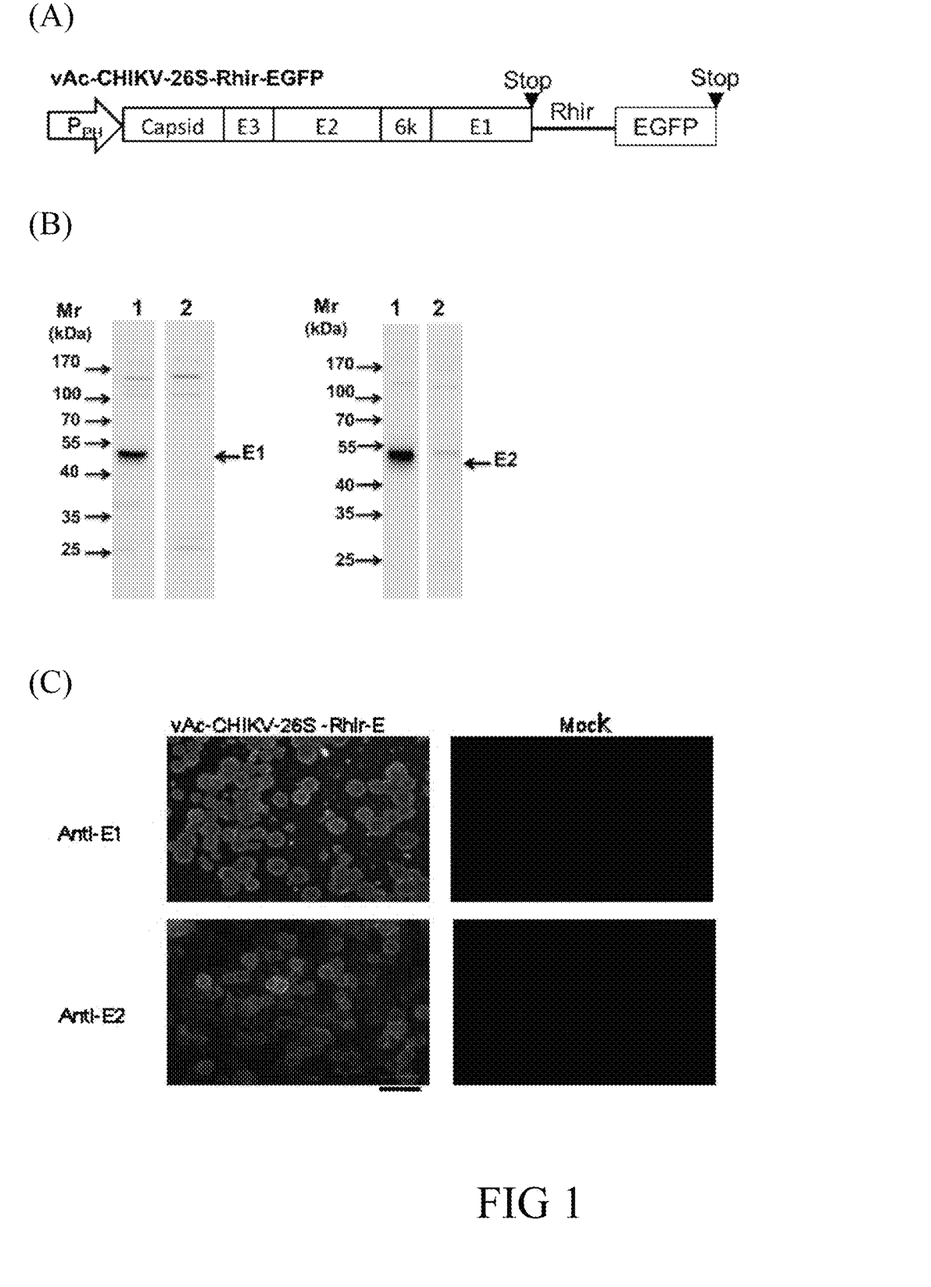
FIG. 1 illustrates the construction and characterization of the recombinant baculovirus of Example 1, in which (A) is a schematic diagram of the recombinant baculovirus vector of example 1.1, (B) are the western blot analyses of anti-E1 and anti-E2 antibodies with proteins extracted from Sf21 cells infected with the recombinant baculovirus vector of example 1.1 (lane 1) or with the mock control (lane 2), and (C) are immunofluorescent images of anti-E1 and anti-E2 antibodies with Sf21 cells infected with the recombinant vector of example 1.1 or with the mock control.

To verify the expression of CHIKV structural proteins, specifically, E1 and E2, on the envelop of the recombinant baculovirus of example 1.1, the anti-E1 and anti-E2 antibodies were respectively mixed with proteins extracted from the host Sf21 cells, and binding was confirmed by western blot analysis (FIG. 1, panel B).

Similarly, when the anti-E1 and anti-E2 antibodies were respectively added to the culture medium of the vAc-CHIKV26S-Rhir-EGFP infected Sf21 cells, those Sf21 cells producing the recombinant baculovirus of example 1.1, as well as E1 and E2 proteins of CHIKV, would bind with anti-E1 or anti-E2 antibodies, which were subsequently identified by the immunofluorescence signals emitted therefrom (FIG. 1, panel C).

1.3 Detecting Anti-CHIKV Antibodies in Serum Samples

In this example, serum samples from CHIKV or DENV infected human subjects were collected under informed written consent. Each serum samples was then mixed with the recombinant baculovirus of example 1.1 and analyzed by ELISA. Results are depicted in FIG. 2.

Figure 2:
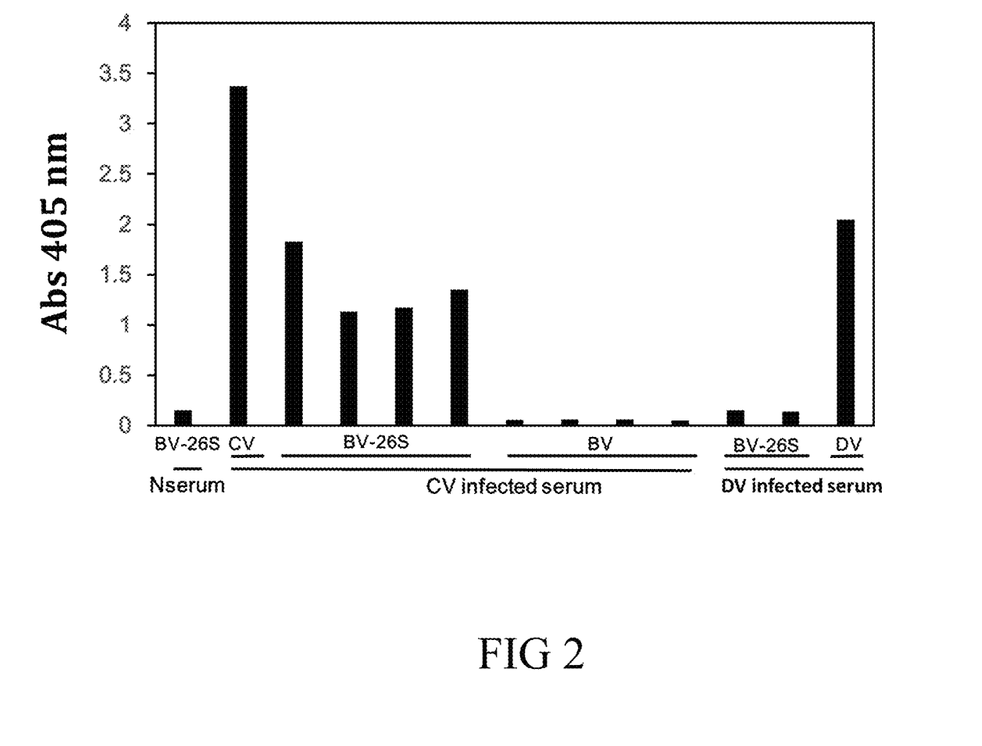
FIG. 2 is a bar diagram depicting the respective binding intensities between the antibodies present in the serum of CHIKV infected subjects and CHIKV per se (denoted as "CV"), the recombinant baculovirus of Example 1.1 (denoted as "BV-26S"), and the recombinant baculovirus without carrying the envelop proteins genes of CHIKV (dented as "BV"), and the respective binding intensities between the antibodies present in the serum of DENV infected subjects with DENV per se (denoted as "DV"), and the recombinant baculovirus of Example 1.1 (denoted as "BV-26S")

For serums of CHIKV infected subjects, positive bindings were found with CHIKV per se (which is denotes as "CV" in FIG. 2) or with the recombinant baculovirus of example 1.1 (which is denoted as "BV-26S" in FIG. 2), while minor or negligible binding was observed with the recombinant baculovirus that did not express the envelop proteins of CHIKV (which is denoted as "BV" in FIG. 2).

As to the serums obtained from DENV infected human subjects, positive binding was found with DENV (which is denoted as "DV" in FIG. 2), but not with the recombinant baculovirus of example 1.1; the result confirms that the recombinant baculovirus of example 1.1 specifically recognizes antibodies in serums of CHIKV infected subjects.

Figure 3:
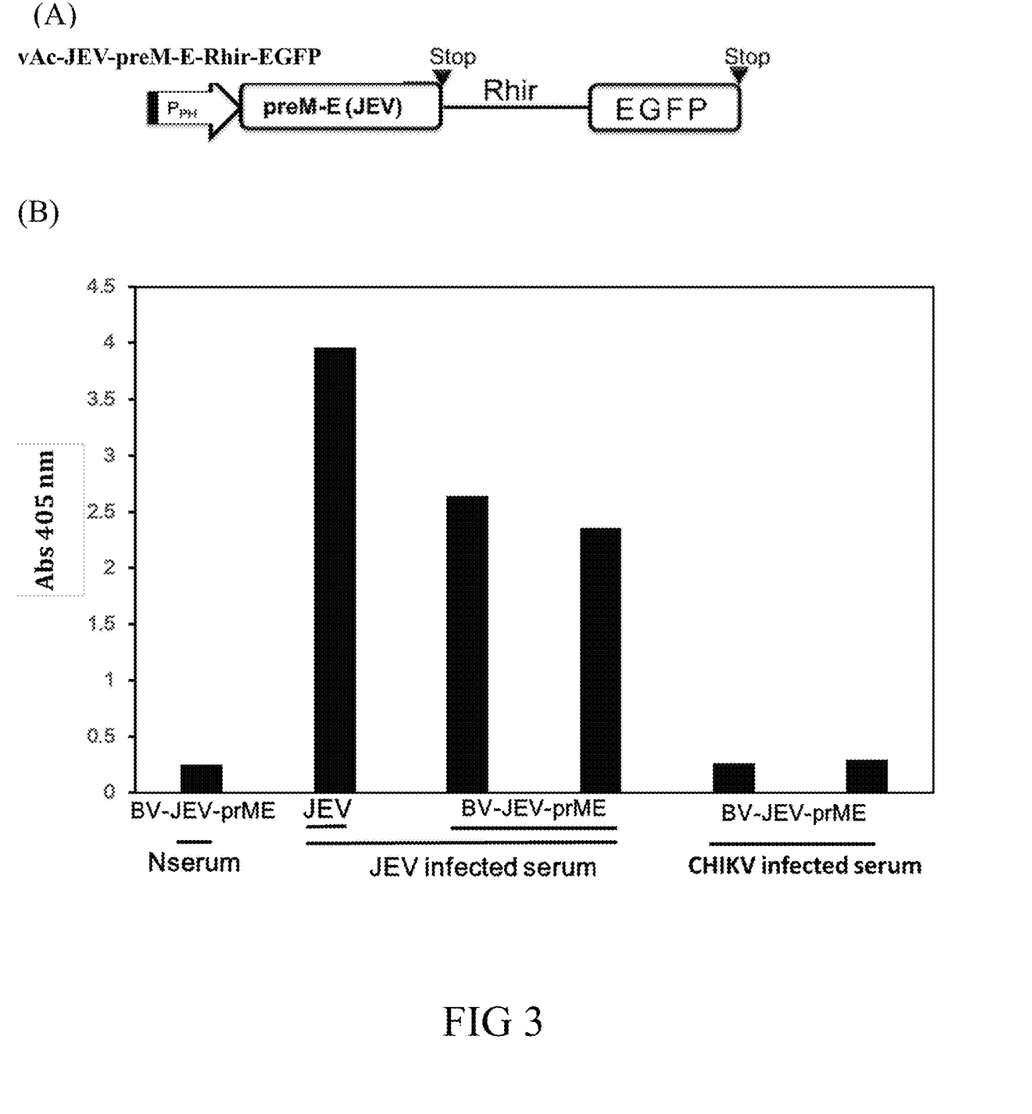
FIG. 3 illustrates the construction and characterization of the recombinant baculovirus of Example 2, in which (A) is a schematic diagram of the recombinant baculovirus vector of example 2.1, and (B) is a bar diagram depicting the respective binding intensities between the anti-JEV antibodies present in the serum of two JEV infected subjects and JEV per se (denoted as "JEV"), and the recombinant baculovirus of Example 2.1 (denoted as "BV-JEV-PrME"); and the respective binding intensities between the anti-CHIKV antibodies present in the serum of CHIKV infected subjects with the recombinant baculovirus of Example 2.1 (denoted as "BV-JEV-PrME")

Example 2 Detecting Anti-JEV Antibodies by Use of a Recombinant Baculovirus Having JEV Viral Proteins Expressed Thereon 2.1 Construction and Characterization of vAc-JEV-preM-E-Lir-EGFP The recombinant baculovirus vectors of this example were respectively constructed in accordance with similar procedures as described in example 1.1, except the full-length cDNA of the CHIKV 26S subgenomic RNA was replaced by the cDNA of JEV virus E RNA (FIG. 3, panel A). Recombinant viruses were then collected and verified by viral DNA sequencing.

2.2 Detecting Anti-JEV Antibodies in Serum Samples of JEV Infected Subjects

Similar to procedures described in example 1.3, the recombinant baculovirus of example 2.1 bond with anti-JEV antibodies in serums samples collected from two JEV infected subjects, but not with serums samples collected from two CHIKV infected patients (FIG. 3, panel B).

Figure 4:
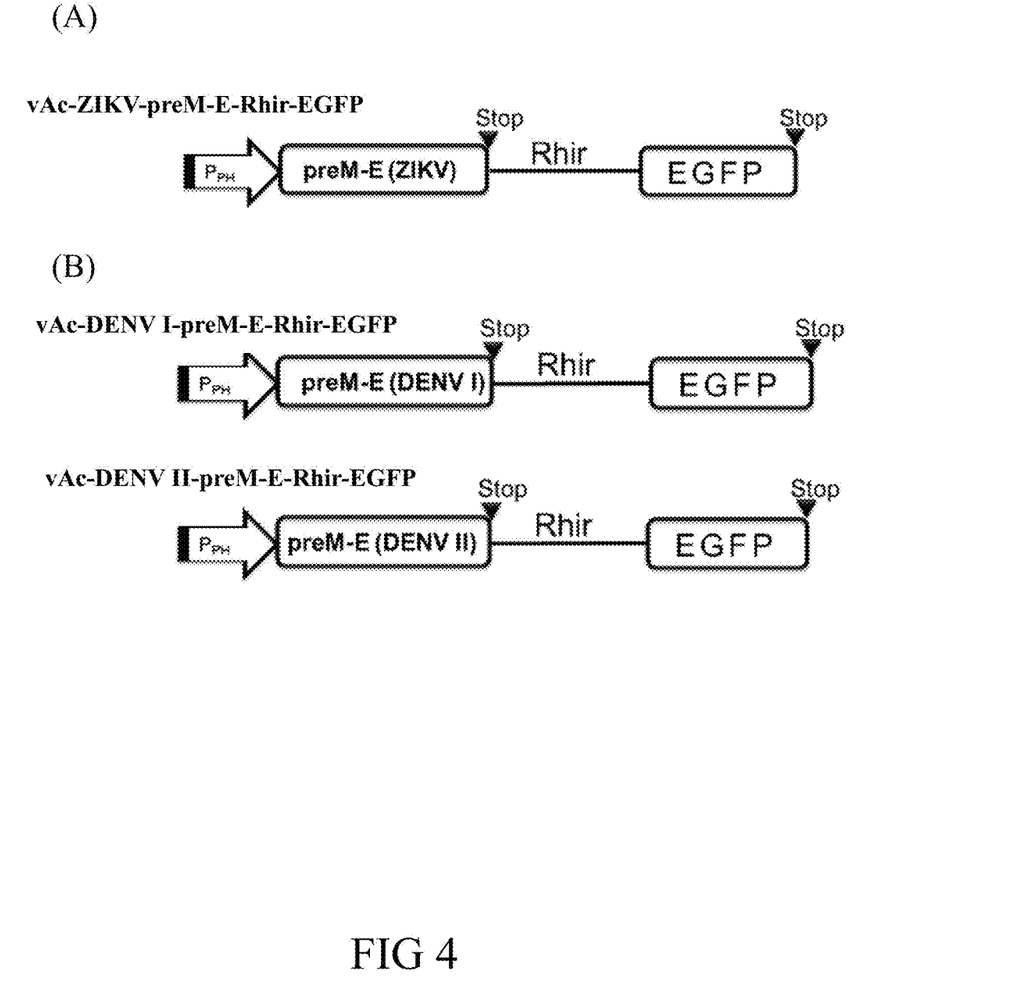
FIG. 4 are schematic diagrams respectively depicting the recombinant baculovirus vectors of (A) example 3.1, and (B) example 4.1 of the present disclosure.

Example 3 Detecting Anti-ZIKV Antibodies by Use of a Recombinant Baculovirus Having ZIKV Viral Proteins Expressed Thereon 3.1 Construction and Characterization of vAc-ZIKV-C-preM-E-Lir-EGFP The recombinant baculovirus vector of this example was constructed in accordance with similar procedures as described in example 1.1, except the full-length cDNA of the CHIKV 26S subgenomic RNA was replaced by the cDNA of Zika virus E RNA (FIG. 4, panel A). Recombinant viruses were then collected and verified by viral DNA sequencing.

It is expected that the thus constructed recombinant baculovirus will be recognized by anti-E antibody of ZIKV.

4.2 Detecting Anti-ZIKV Antibodies in Serum Samples

Similar to procedures described in example 1.3, the recombinant baculovirus of example 4.1 are expected to bind with antibodies in serums samples collected from ZIKV infected subjects, but not with serums samples collected from other arthropod-borne virus (i.e., other than ZIKV) infected subjects.

Example 5 Detecting Anti-DENV Antibodies by Use of a Recombinant Baculovirus Having DENV Viral Proteins Expressed Thereon 5.1 Construction and Characterization of vAc-DENV1-C-preM-E-Lir-EGFP and vAc-DENV2-preM-E-Lir-EGFP The recombinant baculovirus vectors of this example were respectively constructed in accordance with similar procedures as described in example 1.1, except the full-length cDNA of the CHIKV 26S subgenomic RNA was replaced by the cDNA of Type I or II DENV virus E RNA (FIG. 4, panel B). Recombinant viruses were then collected and verified by viral DNA sequencing.

It is expected that the recombinant baculoviruses of example 3.1 will be recognized by anti-E antibody of type I or II DENV.

4.2 Detecting Anti-DENV Antibodies in Serum Samples

Similar to procedures described in example 1.3, the recombinant baculovirus of example 4.1 are expected to bind with antibodies in serums samples collected from type I or II DENV infected subjects, but not with serums samples collected from other arthropod-borne virus (i.e., other than type I or II DENV) infected subjects.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of detecting an antibody against an arthropod-borne virus in a biological sample, comprising:
    mixing the biological sample with a recombinant baculovirus having a viral protein of the arthropod-borne virus expressed thereon, wherein the arthropod-borne virus is Chikungunya virus (CHIKV), and the viral protein comprises E1, E2, and E3; and
    detecting a complex formed between the recombinant baculovirus and the antibody against the arthropod-borne virus in the biological sample, in an immunological assay.

2. The method of claim 1, wherein the antibody is an IgM or IgG.

3. The method of claim 2, wherein the immunological assay is an enzyme-linked immunosorbent assay (ELISA).

4. The method of claim 3, wherein the biological sample is selected from the group consisting of a whole blood sample, a plasma sample, a serum sample, a urine sample, a mucus sample, and purified or filtered forms thereof.

* * * * *